US00PP23247P2

(12) United States Plant Patent
Donahue

(10) Patent No.: US PP23,247 P2
(45) Date of Patent: Dec. 11, 2012

(54) ***LANTANA* PLANT NAMED 'ELEORAN'**

(50) Latin Name: *Lantana camara*
Varietal Denomination: ELEORAN

(76) Inventor: Mitch Donahue, Indian Trail, NC (US)

( * ) Notice: Subject to any disclaimer, the term of this patent is extended or adjusted under 35 U.S.C. 154(b) by 0 days.

(21) Appl. No.: 13/136,115

(22) Filed: Jul. 22, 2011

(51) Int. Cl.
*A01H 5/00* (2006.01)

(52) U.S. Cl. ..... Plt./227

(58) Field of Classification Search ..... Plt./227
See application file for complete search history.

*Primary Examiner* — June Hwu
*Assistant Examiner* — Louanne Krawczewicz Myers
(74) *Attorney, Agent, or Firm* — Cassandra Bright

(57) ABSTRACT

A new and distinct *Lantana* cultivar named 'ELEORAN' is disclosed, characterized by a short, dense plant habit. The new variety produces light orange flowers held just above the top of the canopy of the plant. Plants are highly floriferous and resist stretching under dense growing conditions. The new variety is a *Lantana*, normally produced as an outdoor garden or container plant.

4 Drawing Sheets

Figure 1:
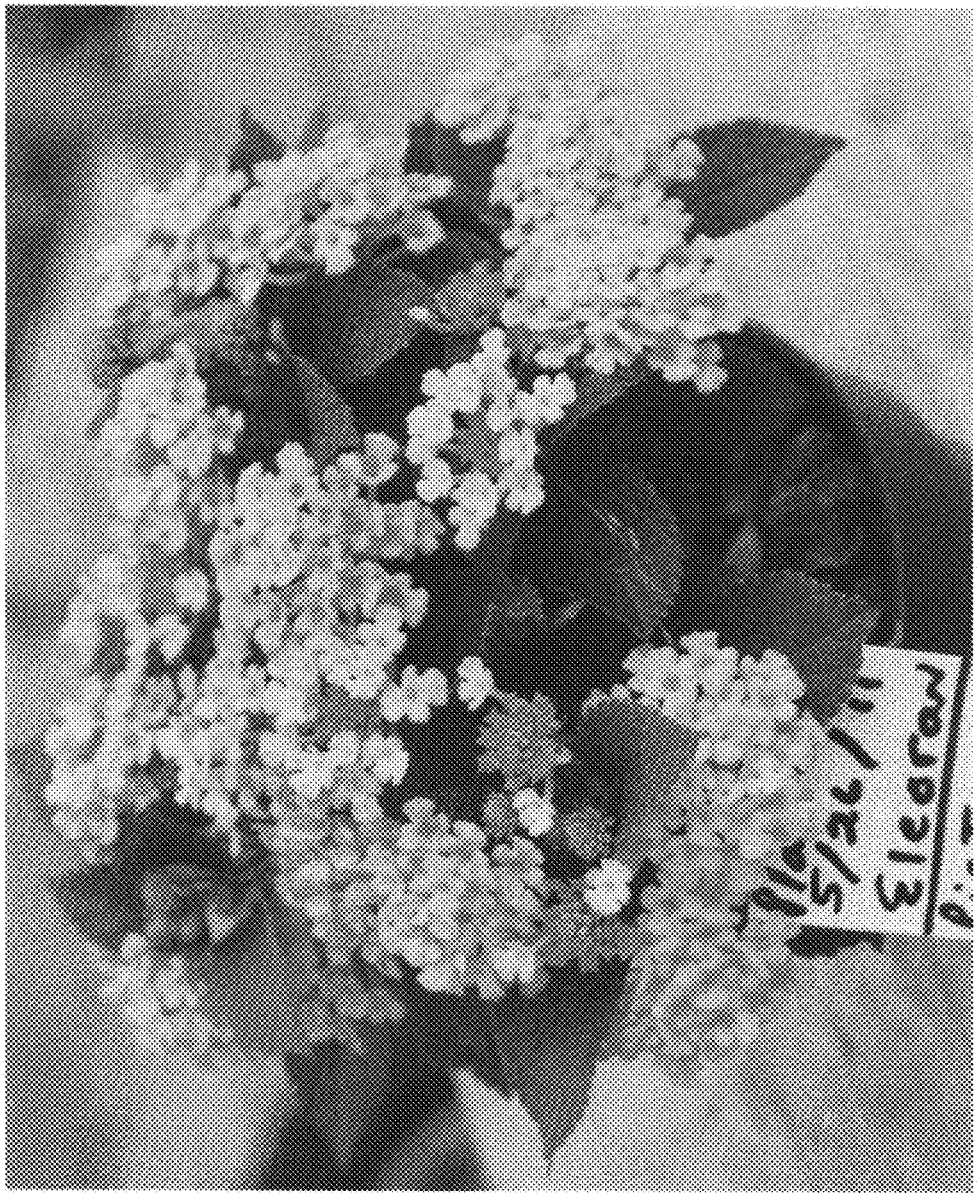

Latin name of the genus and species: *Lantana camara.*
Variety denomination: 'ELEORAN'.

BACKGROUND OF THE INVENTION

The new *Lantana* cultivar is a product of a planned breeding program conducted by the inventor, Mitch Donahue, a citizen of the United States. The objective of the breeding program was to produce new *Lantana* varieties for ornamental commercial applications. The cross resulting in this new variety was made during 2009 at a commercial nursery in Indian Trail, N.C.

The new variety is the result of an open pollination, the parent varieties are unknown *Lantana camara* plants. The new variety was discovered in June 2010 by the inventor in a trial field of seedlings resulting from the 2009 crossing, at the commercial nursery in Indian Trail, N.C.

Asexual reproduction of the new cultivar 'ELEORAN' by vegetative cuttings was first performed at a commercial greenhouse in Indian Trail, N.C. in July 2010. Subsequently, at least 5 generations have been produced, and have shown that the unique features of this cultivar are stable and reproduced true to type in successive generations.

SUMMARY OF THE INVENTION

The cultivar 'ELEORAN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ELEORAN' These characteristics in combination distinguish 'ELEORAN' as a new and distinct *Lantana* cultivar:

1. Very short, dense plant habit
2. Unique light orange flower color
3. Highly floriferous
4. Flowers held just above foliage plane.

5. Plants do not stretch, or develop long internodes, including under dense growing conditions or when grown in small pots.

COMMERCIAL COMPARISON

Plants of the new cultivar 'ELEORAN' are comparable to the variety *Lantana camara* 'Sherbet', unpatented. The two *Lantana* varieties are similar in most horticultural characteristics however, the new variety 'ELEORAN' differs in having lighter orange colored flowers than the comparator variety. Additionally plants of 'ELEORAN' are much shorter and more floriferous than plants of 'Sherbet'.

Plants of the new cultivar 'ELEORAN' are comparable to the commercial variety *Lantana* 'Bante Oransun' U.S. Plant Pat. No. 19,078. The two *Lantana* varieties are similar in most horticultural characteristics however, plants of the new variety 'ELEORAN' are shorter than 'Bante Oransun'. Additionally variety 'ELEORAN' differs in having darker flower buds, and an inflorescence that is more completely orange with age. Foliage differs in that 'ELEORAN' has a different foliage appearance, with shorter leaves that are flat. 'ELEORAN' has also shown to occasionally produce large amounts of seed, a characteristic not observed by the inventor in 'Bante Oransun'. Comparative photos from an independent trial are provided with this application.

BRIEF DESCRIPTION OF THE PHOTOGRAPHS

FIG. 1: Illustrates in full color a closeup view of blooms and buds.

Figure 2:
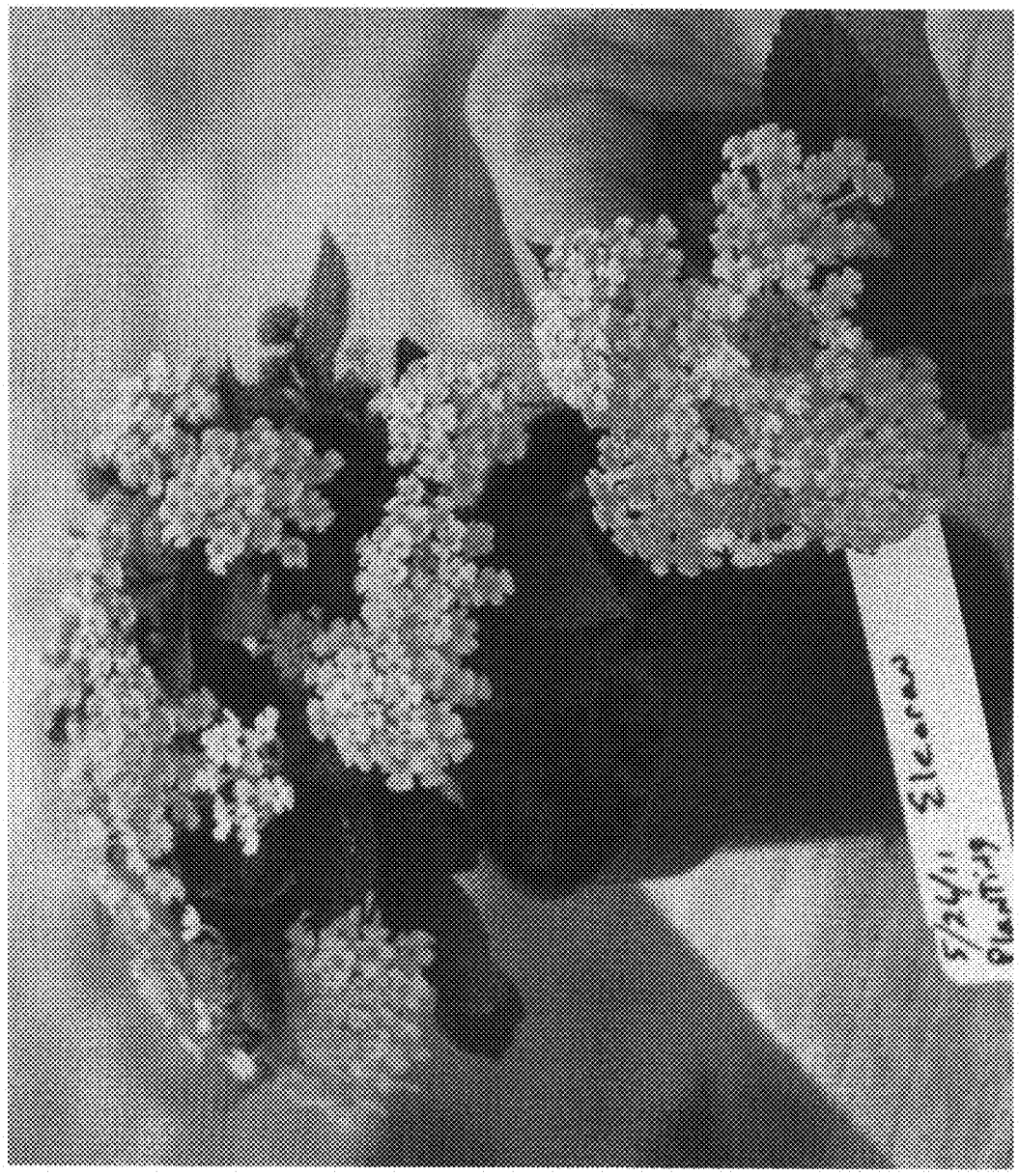

FIG. 2: Illustrates in full color the floriferous nature of 'ELEORAN' in a 4" pot at 8 weeks old from a rooted cutting.

Figure 3:
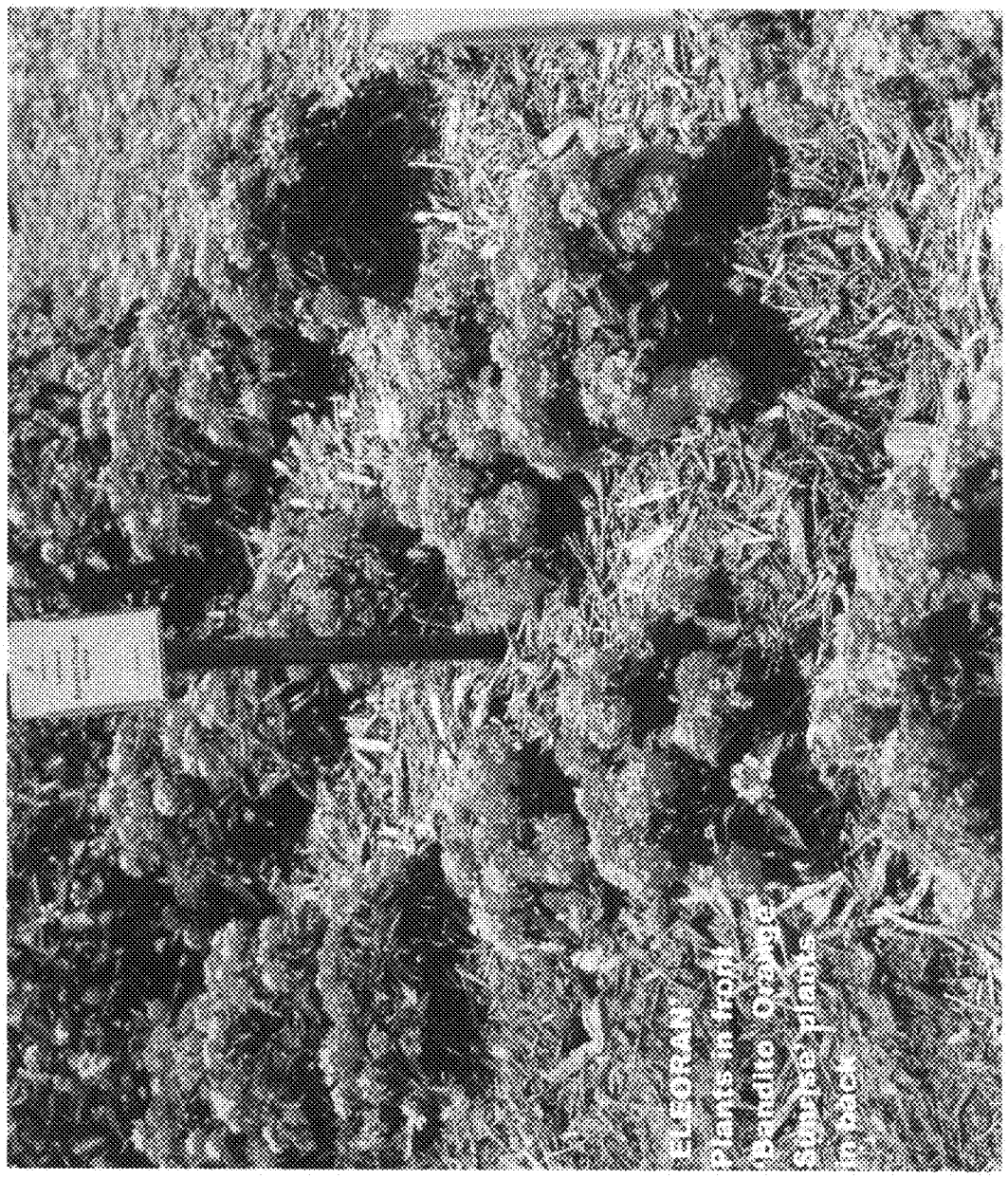

FIG. 3: Shows a comparison of plants of 'ELEORAN' with 'Bante Oransun' at an independent outdoor field trial in North Carolina. Plants are the same age. The shorter overall plant habit of 'ELEORAN' is illustrated.

Figure 4:
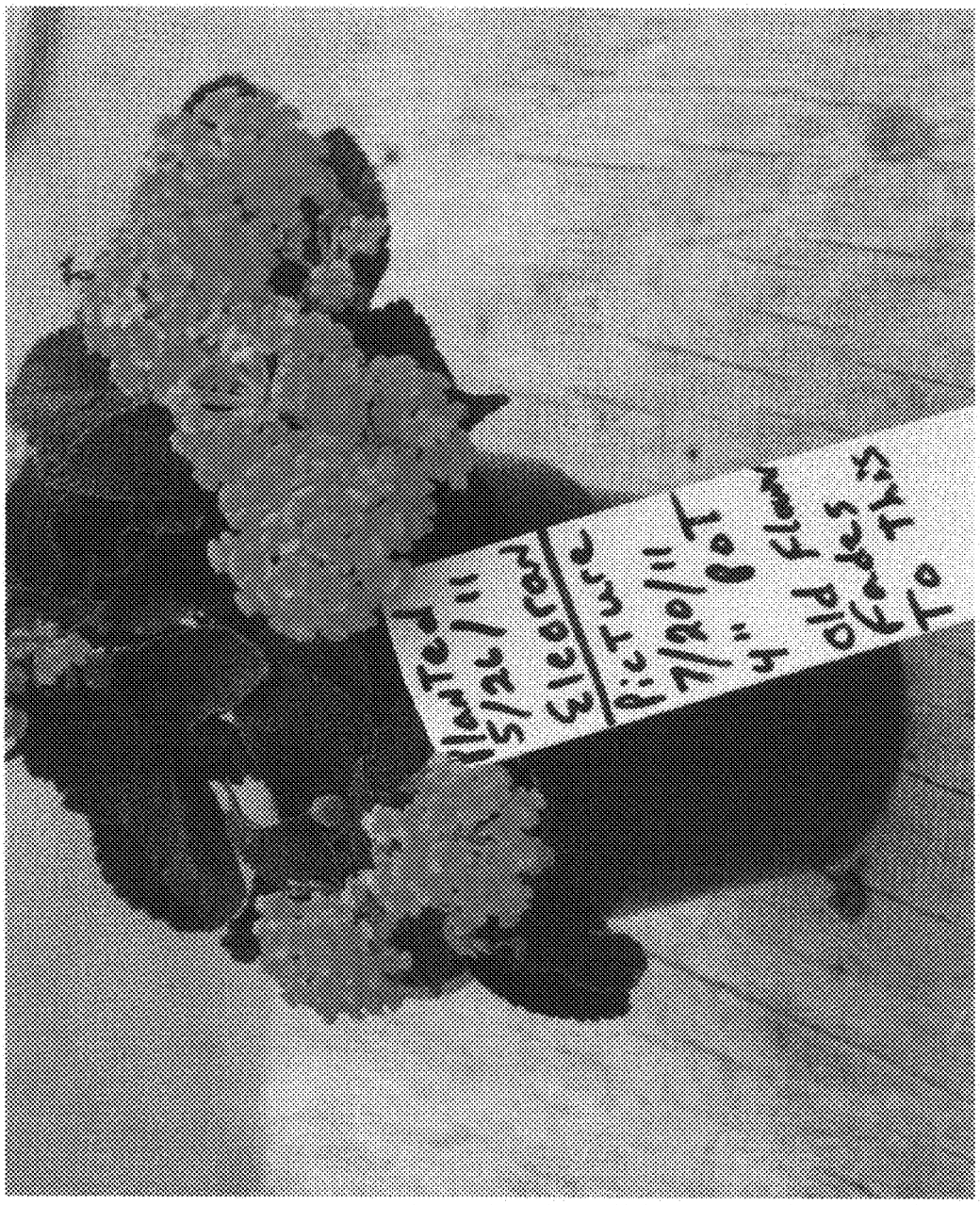

FIG. 4: Illustrates in full color the deep orange coloration of aging flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'ELEORAN' plants grown 8 weeks outdoors during spring in Indian Trail, N.C. The growing temperature ranged from 14° C. to 20° C. during the night and from 22° C. to 35° C. during the day. General light conditions are bright, normal sunlight. Measurements and numerical values represent averages of typical plant types.

Botanical classification: *Lantana camara* 'ELEORAN'.

PROPAGATION

Time to initiate roots: 20 to 24 days at approximately 15° C.

Root description: Fibrous.

PLANT

Growth habit: Upright and mounding.

Pot size of plant described: 10 cm.

Height: 10 cm. to top of flowering plane, 8 cm to top of foliar plane.

Plant spread: 16 cm.

Growth rate: Slower than typical of *Lantana*.

Branching characteristics:

*Length of primary lateral branches.*—7 cm.

Diameter of lateral branches.—0.2 cm.

Quantity of primary lateral branches: 2 main with ability to branch at each node.

Characteristics of primary lateral branches:

*Form*.—Square.

*Diameter*.—0.2 cm.

*Color*.—Near RHS Greyed-Green 195B.

*Texture*.—Moderately Pubescent.

*Strength*.—Strong.

Internode length: 1.5-1.8 cm.

FOLIAGE

*Arrangement*.—Opposite.

*Quantity*.—Approximately 8-10 per branch.

*Average length*.—5 cm.

*Average width*.—2.6 cm.

*Shape of blade*.—Ovate.

*Apex*.—Acute.

*Base*.—Obtuse.

*Margin*.—Slightly serrated.

*Texture of top surface*.—Slightly scabrous.

*Texture of bottom surface*.—Glabrous.

*Pubescence*.—Covered with hairs.

*Aspect*.—Flat.

*Fragrance*.—Moderate typical *Lantana* fragrance.

*Color*.—Young foliage upper side: Near RHS Green 139A. Young foliage under side: Near RHS Green 143A. Mature foliage upper side: Near RHS Green 139A. Mature foliage under side: Near RHS Green 141C.

*Venation*.—Type: Pinnate. Venation color upper side: Near RHS Green 141C. Venation color under side: Near RHS Green 142B.

*Petiole*.—Length: 0.9 cm. Diameter: 0.1 cm. Color: Near RHS Green 141C. Texture: Moderately Covered with Short Hairs.

FLOWER

Natural flowering season: Year Round in Warm Climate.

Days to flowering from rooted cutting: 28.

Inflorescence and flower type and habit: Corymb.

Rate of flower opening: 1 to 2 days from bud to fully opened flower.

Flower longevity on plant: 1 week after maturity.

Persistent or self-cleaning: Self Cleaning.

Flower fragrance: Mild.

Overall inflorescence size:

*Height*.—Approximately 2 cm.

*Diameter*.—Approximately 3 cm.

Flowers per inflorescence: Average 20.

Umbels per lateral stem: Average 8.

Buds and individual flowers per plant: Average 600 flowers and buds per plant in full bloom.

Individual flower size:

*Height*.—Approximately 1 cm (Including Corolla Tube).

*Diameter*.—Approximately 0.7 cm.

Bud:

*Shape*.—Square Pillow Shaped.

*Length*.—0.5 cm (Including Corolla Tube).

*Diameter*.—0.3 cm.

*Color*.—Near RHS Red 53B.

Corolla:

*Petals/lobes*.—Number: 5. (2 upper petals fused and appear as one. All 5 are fused at base to form a corolla tube.) Petal Lobes: Shape: Obdeltoid. Lobe Apex: Mucronate. Lobe Depth: Approximately 0.15 cm, or approximately 40% of length. Length: Upper: 0.4 cm Lateral: 0.3 cm Lower: 0.4 cm. Width: Upper 0.4 cm Lateral: 0.3 cm Lower: 0.6 cm. Shape: Salverform. Aspect: Slightly Cup Shaped with a long slender tube. Margin: Entire — Slightly Ruffled. Texture: Smooth, all surfaces. Color: When opening: Upper Petals: Upper surface: Near RHS Yellow-Orange 17C. Lower surface: Top Petals: Near RHS Yellow-Orange 21C. Bottom Petals: Upper Surface: Near RHS Yellow-Orange 21C. Lower Surface: Near RHS Yellow-Orange 21C. Lateral Petals: Upper Surface: Near RHS Red 39A. Lower Surface: Near RHS Red 39A. Fully opened: Upper surface: All Petals: Yellow-Orange 17A RHS with mingled Orange-Red 33A from throat of tube. Lower surface: Top Petals: Near RHS Yellow-Orange 21C with thin stripe of Red 39A where top two petals are fused to appear as one. Bottom Petals: Near RHS Yellow-Orange 21C. Lateral Petals: Mostly Red 40C except Yellow-Orange 21C near corolla tube. Old flowers fade to Red 46C on upper side. Lower side Red 38D top and bottom petals. 2 Lateral Petals — Lower Red-Purple 58A.

*Throat/tube*.—Throat Color: Near RHS Yellow-Orange 21A. Tube Color: Near RHS Yellow 13A at top to 8C.

*Tube length*.—Approximately 0.8 cm.
*Tube width*.—Approximately 0.25 cm.
*Tube texture, inner surface*.—Glabrous.
*Tube texture, outer surface*.—Glabrous.

Calyx/sepals:
*Form*.—5 Fused Sepals Form a Tube around base of each floret.
*Length*.—0.2 cm.
*Diameter*.—0.15 cm.
*Sepal shape*.—Tube Shaped.
*Sepal margin*.—Sides are fused leaving small tips sticking up.
*Sepal texture, upper and lower surfaces*.—Pubescent (Slightly).
*Sepal color*.—Upper surface: Near RHS Yellow-Green 145A. Lower surface: Near RHS Yellow-Green 145A.

Flower bracts/inflorescence bracts:
*Length*.—Approximately 0.5 cm.
*Width*.—Approximately 0.1 cm.
*Shape*.—Lanceolate.
*Apex*.—Acute.
*Margin*.—Entire.
*Texture*.—Upper (inner) and lower (outer) surfaces: Densely Pubescent.
*Color*.—Upper (Inner): Near RHS Yellow-Green 144A at base changes to Green 137A at approximately mid length to tip. Lower (Outer): Near RHS Green 143C at base changes to Green 137A at approx mid length.

Peduncles:
*Length*.—Approximately 1.6 cm-3.2 cm.
*Diameter*.—Approximately 0.1 cm.
*Angle*.—About 45 degrees.
*Strength*.—Strong.
*Texture*.—Densely Pubescent.
*Color*.—Near RHS Green 143B. Pedicels are not present; the corolla tubes are directly connected to the top of the peduncle.

REPRODUCTIVE ORGANS

Stamens:
*Number* (*per flower*).—4.
*Filament length*.—0.2 cm.
*Anthers*.—Shape: Ovate. Length: 0.1 cm. Color: 200B RHS.

Pollen:
*Color*.—Near RHS Yellow-Orange 16C.
*Amount*.—Sparse to None.

Pistils:
*Quantity per flower*.—1.
*Length*.—0.4 cm.
*Styles*.—Length: 0.2 cm. Color: Closest to Green-Yellow 1D.
Ovary color.—Near RHS Green 138 B RHS.
*Stigma*.—Shape: Funnel. Color: Near RHS Yellow-Green 144A.

OTHER CHARACTERISTICS

Seeds and fruits:
*Seed diameter*.—3 mm.
*Color*.—Near RHS Brown 200A.
*Seed quantity*.—Abundant.

Disease/pest resistance: Neither resistance nor susceptibility to pathogens and pests common to *Lantana* have been observed.

Temperature tolerance: The new variety tolerates temperatures between 0 to 40° C.

What is claimed is:

1. A new and distinct cultivar of *Lantana* plant named 'ELEORAN' as herein illustrated and described.

* * * * *